United States Patent [19]

McAllister

[11] Patent Number: 5,037,745

[45] Date of Patent: * Aug. 6, 1991

[54] PLASMID FOR THE OVERPRODUCTION OF BACTERIOPHAGE T3 RNA POLYMERASE, TRANSCRIPTION VECTORS THAT CARRY A PROMOTER RECOGNIZED BY ITS POLYMERASE, GENE CODING FOR T3 RNA POLYMERASE AND APPLICATION OF THESE PLASMIDS

[75] Inventor: William T. McAllister, Metuchen, N.J.

[73] Assignee: University of Medicine and Dentistry of New Jersey, Newark, N.J.

[ * ] Notice: The portion of the term of this patent subsequent to May 21, 2008 has been disclaimed.

[21] Appl. No.: 846,931

[22] Filed: Apr. 1, 1986

[51] Int. Cl.$^5$ .......................... C12N 7/01; C12N 9/12; C12N 15/00; C12N 15/10

[52] U.S. Cl. .................... 435/91; 435/320.1; 435/6; 435/172.3; 435/194; 435/235.1; 935/31; 935/17

[58] Field of Search ................. 435/172.3, 6, 91, 320, 435/194, 235; 536/27; 935/29, 14, 31, 41, 16, 72, 73

[56] References Cited

U.S. PATENT DOCUMENTS 4,766,072 8/1988 Jendrisak et al. .................... 435/91

OTHER PUBLICATIONS

Bluescribe Advertisement, 1985.
BRL Catalogue, 1985.
McGraw, N. et al, *Nuc Acid Res*, vol. 13, pp. 6753–6766, Sep. 1985.
Melton, D. et al, *Nuc. Acids Res.*, vol. 12, pp. 7035–7056, 1984.
Axelrod, V. et al, *Biochemistry*, vol. 24, pp. 5716–5723, Oct. 1985.
Pharmacia Advertisement in *Nature*, vol. 317, Oct. 1985.
Adhya, S. et al, *Proc. Natl. Acad. Sci.*, vol. 78, pp. 147–151, 1981.
Bailey, J. et al., *Proc. Natl. Acad. Sci.*, vol. 80, pp. 2814–2818, May, 1983.

*Primary Examiner*—Richard A. Schwartz
*Assistant Examiner*—S. L. Nolan
*Attorney, Agent, or Firm*—Weiser & Stapler

[57] ABSTRACT

A dual phage RNA polymerase promoter having a polylinker with at opposite ends, a T3 phage RNA polymerase promoter and a phage RNA polymerase promoter, like T7; the promoters are linked to the polylinker in opposite orientation. A recombinant DNA vector containing a T3 phage RNA polymerase promoter and a different phage RNA polymerase promoter; the promoters are linked to a polylinker sequence in opposite orientation. A kit including a T3 promoter and containing appropriate components for synthesizing RNA transcripts that are complementary to either strands of a cloned DNA sequence, and for other applications. Gene coding for T3 RNA polymerase, a vector containing the gene and transformed microorganisms.

22 Claims, 7 Drawing Sheets

```
    1
T3  GATGAGGTGCGCATTGTGGGGCAAACCGTTACACATAGACGCATACCTTGACAAGCGTCT
       :: :   :::: ::              :  :::::::                  :
T7  CCGGATGGCTATCGCTAATGGTCTTACGCTCAACATTGATAAGCAACTTGACGCAATGTT

61
T3  ACAAGGCTGATAGAGTCTTTTCTTACAGGTCATCATGAGGTGGCCTGAATAGGAACGATT
     :  :::::::  ::::::  ::::::::::::::  :   ::::::::::::  ::::::
T7  AATGGGCTGAT--AGTCTTATCTTACAGGTCATCTGCGGGTGGCCTGAATAGGTACGATT

120
T3  TATTCAC--AATGAGGTAAGCAATGAACATCATCGAAAACATCGAAAAGAATGACTTCTC
     :: : ::    : ::::: :   ::::::::: ::      ::::::: ::::::::::::
T7  TACTAACTGGAAGAGGCACTAAATGAACACGAT---TAACATCGCTAAGAACGACTTCTC

180
T3  AGAAATCGAACTGGCTGCTATCCCGTTCAACACACTGGCTGACCACTACGG-AAGCGCCT
     :: :::::::::::::::::::::::::::::: ::::::::::::  ::::  ::::  :
T7  TGACATCGAACTGGCTGCTATCCCGTTCAACACTCTGGCTGACCATTACGGTGAGCG-TT

240
T3  TGGCTAAAGAGCAGTTGGCTTTAGAACATGAGTCTTATGAGCTAGGCGAGCGCCGCTTCC
    : :::  ::  :::::::::  :: ::::::::::::: ::: :  :: ::  :::::::
T7  TAGCTCGCGAACAGTTGGCCCTTGAGCATGAGTCTTACGAGATGGGTGAAGCACGCTTCC

300
T3  TCAAGATGCTTGAGCGTCAAGCGAAAGCTGGTGAGATTGCAGACAACGCAGCCGCTAAGC
    :::::::  ::::::::::   :::  :::::::::  :::  :: ::::: ::::: ::::
T7  GCAAGATGTTTGAGCGTCAACTTAAAGCTGGTGAGGTTGCGGATAACGCTGCCGCCAAGC

360
T3  CGTTACTCGCTACGCTTCTCCCTAAGTTAACCACACGTATCGTCGAGTGGCTCGAAGAGT
    :  :  ::  ::::  ::  ::::::::::: : :     :::: :::  ::: :   :: ::
T7  CTCTCATCACTACCCTACTCCCTAAGATGATTGCACGCATCAACGACTGGTTTGAGGAAG

420
T3  ACGCATCGAAGAAAGGCCGCAAGCCTAGCGCATACGCACCGCTCCAGTTACTCAAGCCGG
     : : :::   :::   :::        ::  ::   : ::: :        ::  ::   : :::::::::
T7  TGAAAGCTAAGCGCGGCAAGCGCCCGACAGCCTTCCAGTTCCTGCAAGAAATCAAGCCGG

480
T3  AGGCCTCCGCGTTTATCACCCTGAAAGTTATCCTTGCGTCACTAACCAGTACGAACATGA
     : :::   :::: ::::::: ::  :    :: :: :::::::::: :   ::: :
T7  AAGCCGTAGCGTACATCACCATTAAGACCACTCTGGCTTGCCTAACCAGTGCTGACAATA

540
T3  CAACCATTCAGGCCGCTGCTGGTATGCTGGGGAAAGCCATTGAGGACGAGGCACGATTTG
    ::::: :::::::  ::   :    : ::  ::::::::::::::::::::: :::  :: :
T7  CAACCGTTCAGGCTGTAGCAAGCGCAATCGGTCGGGCCATTGAGGACGAGGCTCGCTTCG

600
T3  GGCGCATCCGTGACCTAGAAGCGAAGCACTTCAAGAAGCACGTTGAGGAACAGCTTAACA
    :  ::  :::::::::::  :::::::::::::::::::::   :::::::::::  :: ::::
T7  GTCGTATCCGTGACCTTGAAGCTAAGCACTTCAAGAAAAACGTTGAGGAACAACTCAACA

660
T3  AGCGCCACGGGCAAGTCTACAAGAAAGCATTTATGCAGGTGGTCGAGGCCGATATGATTG
    :::::    ::::: ::::::::::::::::::::::  ::::::::::  :::: : :::  :
T7  AGCGCGTAGGGCACGTCTACAAGAAAGCATTTATGCAAGTTGTCGAGGCTGACATGCTCT

720
T3  GTCGAGGTCTGCTTGGTGGCGAGGCGTGGTCTAGCTGGGATAAAGAAACCACGATGCACG
     :     :::::  ::  :::::::::::::::::  ::: :::: ::: ::: :  ::  ::  :
T7  CTAAGGGTCTACTCGGTGGCGAGGCGTGGTCTTCGTGGCATAAGGAAGACTCTATTCATG
```

FIG.4 CONT.'

```
       780        790       800       810       820       830
T3  TAGGGATTCGCCTGATTGAAATGCTGATTGAATCCACGGGTCTGGTGGAATTACAGCGCC
    ::::  : :::   :: ::  :::::  :::::  :: :: :: :::    :::: ::::
T7  TAGGAGTACGCTGCATCGAGATGCTCATTGAGTCAACCGGAATGGTTAGCTTACACCGCC

840
T3  ACAACGCAGGTAACGCAGGCTCTGACCATGAGGCACTGCAACTGGCCCAAGAGTACGTGG
    : ::  :: ::      : :::      :::   ::::: :   :::: ::  :: :::: :
T7  AAAATGCTGGCGTAGTAGGTCAAGACTCTGAGACTATCGAACTCGCACCTGAATACGCTG

900
T3  ACGTATTAGCGAAGCGTGCAGGCGCTCTGGCGGGTATCTCTCCGATGTTCCAGCCGTGTG
    : :    : :: :  ::::::::  ::  :::::  ::  ::::::::::::::  :: :: :
T7  AGGCTATCGCAACCCGTGCAGGTGCGCTGGCTGGCATCTCTCCGATGTTCCAACCTTGCG

960
T3  TCGTACCGCCGAAACCTTGGGTAGCAATCACAGGGGGCGGCTATTGGGCTAACGGTCGCA
    : :: :: ::  :: :: ::  :::    :  :: ::  :: :: :::::::::::::::::::
T7  TAGTTCCTCCTAAGCCGTGGACTGGCATTACTGGTGGTGGCTATTGGGCTAACGGTCGTC

1020
T3  GACCTTTGGCACTCGTTCGCACTCACTCTAAGAAGGGCTTGATGCGCTACGAAGACGTTT
    : :::: :::: :: ::  :: ::::::  :::::: :   ::::::::::::::::::::::
T7  GTCCTCTGGCGCTGGTGCGTACTCACAGTAAGAAAGCACTGATGCGCTACGAAGACGTTT

1080
T3  ACATGCCAGAAGTCTACAAGGCTGTGAACCTCGCGCAAAACACCGCATGGAAAATCAACA
    ::::::::   :: ::  :::::  ::  : :::  : ::::::::::::::::::::::::::
T7  ACATGCCTGAGGTGTACAAAGCGATTAACATTGCGCAAAACACCGCATGGAAAATCAACA

1140
T3  AGAAAGTTCTTGCTGTTGTCAATGAGATTGTTAACTGGAAGAATTGCCCGGTAGCAGACA
    ::::::: :: :: :: ::  ::: :   ::    :: ::::::: ::::  ::::: :  ::::
T7  AGAAAGTCCTAGCGGTCGCCAACGTAATCACCAAGTGGAAGCATTGTCCGGTCGAGGACA

1200
T3  TTCCATCGCTGGAGCGCCAAGAGTTACCGCCTAAGCCTGACGACATTGACACCAACGAGG
    : ::  ::  : :::::  ::::  : :::    ::  :: ::::: ::::  :: ::    :
T7  TCCCTGCGATTGAGCGTGAAGAACTCCCGATGAAACCGGAAGACATCGACATGAATCCTG

1260
T3  CAGCGCTCAAGGAGTGGAAGAAAGCCGCTGCTGGTATCTATCGCTTGGACAAGGCACGAG
    :: :::::   : :::::::     :: ::  :::: :  : ::  :::  :::::::::: ::
T7  AGGCTCTCACCGCGTGGAAACGTGCTGCCGCTGCTGTGTACCGCAAGGACAAGGCTCGCA

1320
T3  TGTCTCGCCGTATCAGCTTAGAGTTCATGCTGGAGCAGGCCAACAAGTTCGCAAGTAAGA
    :::::::::::::::::: : ::::::::::::: :::::  :::::  :::::: :: :    : :
T7  AGTCTCGCCGTATCAGCCTTGAGTTCATGCTTGAGCAAGCCAATAAGTTTGCTAACCATA

1380
T3  AAGCAATCTGGTTCCCTTACAACATGGACTGGCGCGGTCGTGTGTACGCTGTGCCGATGT
    : ::  :::::::::::::::::::::::::::::::::::::: ::::  :::::::::  : ::::
T7  AGGCCATCTGGTTCCCTTACAACATGGACTGGCGCGGTCGTGTTTACGCTGTGTCAATGT

1440
T3  TCAACCCGCAAGGCAACGACATGACGAAAGGTCTGCTGACCCTTGCTAAAGGCAAGCCAA
    ::::::::::::::: ::::::: :::::: ::  :: ::  :: ::  :: :: :::::: :: ::::
T7  TCAACCCGCAAGGTAACGATATGACCAAAGGACTGCTTACGCTGGCGAAAGGTAAACCAA

1500
T3  TCGGTGAGGAAGGTTTCTACTGGCTGAAAATCCACGGTGCGAACTGTGCGGGTGTTGATA
    :::::   :::::::::: ::::::::::::::::::::::::: :::::::::::::::: :::: ::::
T7  TCGGTAAGGAAGGTTACTACTGGCTGAAAATCCACGGTGCAAACTGTGCGGGTGTCGATA
```

FIG. 4 CONT.'

```
     1560
T3   AGGTTCCATTCCCGGAGCGCATCGCGTTCATTGAGAAGCACGTAGACGACATTCTGGCTT
     ::::::::  :::: :::::::::::  ::::::::::: :  ::   ::  ::::  ::::::
T7   AGGTTCCGTTCCCTGAGCGCATCAAGTTCATTGAGGAAAACCACGAGAACATCATGGCTT

1620
T3   GCGCTAAAGACCCAATCAATAACACTTGGTGGGCTGAGCAGGATTCACCGTTCTGTTTCC
     :::::::  :::  :  :  ::::::::::::::::::::: :::::  :::::::::: ::::
T7   GCGCTAAGTCTCCACTGGAGAACACTTGGTGGGCTGAGCAAGATTCTCCGTTCTGCTTCC 1680     1690     1700     1710     1720     1730
T3   TCGCGTTTTGCTTCGAGTATGCAGGCGTTACGCACCACGGTCTGAGCTACAATTGCTCTC
     :  :::::  :::::  :::::  ::  ::  ::          :::::::::::: :::::::: :
T7   TTGCGTTCTGCTTTGAGTACGCTGGGGTACAGCACCACGGCCTGAGCTATAACTGCTCCC

1740
T3   TGCCGCTGGCGTTCGACGGGTCTTGCTCTGGTATCCAGCACTTCTCCGCGATGCTCCGCG
     :  ::::::::::::: ::::::::::::::::::::: ::::::::::::::::::::::::::::: :
T7   TTCCGCTGGCGTTTGACGGGTCTTGCTCTGGCATCCAGCACTTCTCCGCGATGCTCCGAG

1800
T3   ATGAGGTAGGCGGTCGTGCGGTTAACCTGCTGCCAAGCGAAACCGTGCAGGACATTTACG
     ::::::::::: :::::  :::::::::: ::::::::::: ::  ::  :::::::::: :::::::::  ::::
T7   ATGAGGTAGGTGGTCGCGCGGTTAACTTGCTTCCTAGTGAAACCGTTCAGGACATCTACG

1860
T3   GCATCGTTGCACAGAAAGTAAACGAGATTCTCAAACAGGATGCAATCAACGGCACGCCTA
     :  :: ::::::   :::::::  :::::::::::: ::   :: :::::::::: ::  ::      ::
T7   GGATTGTTGCTAAGAAAGTCAACGAGATTCTACAAGCAGACGCAATCAATGGGACCGATA

1920
T3   ACGAGATGATTACCGTGACCGACAAGGACACCGGGGAAATCTCAGAGAAGCTCAAACTTG
     ::::  :  :::::::::::::::  :: ::::  :: :::::::::: ::::::   ::::  ::  :
T7   ACGAAGTAGTTACCGTGACCGATGAGAACACTGGTGAAATCTCTGAGAAAGTCAAGCTGG

1980
T3   GAACCTCAACGCTGGCGCAACAGTGGCTGGCATATGGTGTAACCCGTAGCGTAACTAAAC
     :  ::     :  ::::::    ::  :::::::::: ::  :::::::::  ::      :::: ::
T7   GCACTAAGGCACTGGCTGGTCAATGGCTGGCTTACGGTGTTACTCGCAGTGTGACTAAGC

2040
T3   GTTCGGTCATGACGCTGGCTTACGGTTCCAAGGAGTTCGGCTTTCGTCAACAGGTATTGG
     ::::  ::::::::::::::::::::::  ::::: :::::::::::: ::::::::  ::    :::
T7   GTTCAGTCATGACGCTGGCTTACGGGTCCAAAGAGTTCGGCTTCCGTCAACAAGTGCTGG

2100
T3   ATGACACCATTCAGCCTGCAATTGACAGCGGTAAGGGCTTGATGTTCACCCAACCGAACC
     :  ::  ::::::::::::  :: :::::      :::  :::::  ::::::::::  ::::::: :
T7   AAGATACCATTCAGCCAGCTATTGATTCCGGCAAGGGTCTGATGTTCACTCAGCCGAATC

2160
T3   AAGCGGCTGGCTATATGGCTAAGCTGATTTGGGATGCGGTAAGCGTGACCGTAGTTGCAG
     :  ::  ::::::  ::  :::::::::::::::::::::::::  :  ::  :::::::::: ::  ::  ::  :
T7   AGGCTGCTGGATACATGGCTAAGCTGATTTGGGAATCTGTGAGCGTGACGGTGGTAGCTG

2220
T3   CGGTTGAGGCGATGAACTGGCTCAAATCTGCCGCTAAGCTGCTGGCTGCTGAGGTCAAGG
     ::::::::  ::  ::::::::::::::  ::  :::::  ::::::::::::::::::::::::::::::::: :
T7   CGGTTGAAGCAATGAACTGGCTTAAGTCTGCTGCTAAGCTGCTGGCTGCTGAGGTCAAAG

2280
T3   ACAAGAAGACCAAGGAGATTCTGCGCCACCGTTGCGCGGTTCACTGGACTACGCCGGACG
     :::::::::  :::::::::::::::  :  ::::::::: :::::: ::  ::  :::   ::  ::  ::  :
T7   ATAAGAAGACTGGAGAGATTCTTCGCAAGCGTTGCGCTGTGCATTGGGTAACTCCTGATG
```

FIG.4 CONT.'

```
     2340
T3   GCTTCCCGGTCTGGCAGGAATACCGCAAGCCACTCCAGAAGCGTCTCGATATGATTTTCT
     : ::::: ::  ::::::::::::    :::::  : ::::  :::   :  :   :::: :::
T7   GTTTCCCTGTGTGGCAGGAATACAAGAAGCCTATTCAGACGCGCTTGAACCTGATGTTCC

2400
T3   TAGGGCAATTCCGTCTGCAACCGACGATTAATACCCTCAAGGATTCAGGCATTGACGCAC
     :  :: ::  ::::::  :  :: ::  ::  :::::: :::  ::: :::   : :::::: ::::
T7   TCGGTCAGTTCCGCTTACAGCCTACCATTAACACCAACAAAGATAGCGAGATTGATGCAC

2460
T3   ACAAGCAGGAGTCTGGCATCGCTCCTAACTTTGTTCACTCACAGGACGGTAGCCACCTCC
     :::: :::::::::::: ::::::::::::::::::: :::   :: :::::::::::::: :
T7   ACAAACAGGAGTCTGGTATCGCTCCTAACTTTGTACACAGCCAAGACGGTAGCCACCTTC

2520
T3   GCATGACAGTCGTTTATGCTCACGAGAAGTATGGCATTGAGTCCTTTGCGCTCATCCATG
     : : ::: :: :: :  ::  :::::::::::: :: ::  :: ::  ::::: ::  ::  :: :
T7   GTAAGACTGTAGTGTGGGCACACGAGAAGTACGGAATCGAATCTTTTGCACTGATTCACG

2580
T3   ACAGCTTTGGGACTATCCCGGCAGACGCTGGTAAGCTCTTTAAGGCTGTGCGTGAAACGA
     ::  ::: ::  ::  ::::: :::::::  ::  ::  ::  :: :: ::::: ::::: :
T7   ACTCCTTCGGTACCATTCCGGCTGACGCTGCGAACCTGTTCAAAGCAGTGCGCGAAACTA

2640
T3   TGGTTATCACCTATGAGAACAACGATGTGCTGGCAGACTTCTACTCTCAGTTTGCCGACC
     :::::   :::   ::::::   ::::: :::::  :: ::::::     :::::  :: ::::
T7   TGGTTGACACATATGAGTCTTGTGATGTACTGGCTGATTTCTACGACCAGTTCGCTGACC

2700
T3   AGCTACACGAGACCCAACTGGACAAGATGCCTCCGCTTCCGAAGAAAGGAAACCTGAACC
     ::  :  :::::::  : ::: ::::::: ::::: ::::::   ::::: :::::   :::: :::::::
T7   AGTTGCACGAGTCTCAATTGGACAAAATGCCAGCACTTCCGGCTAAAGGTAACTTGAACC

2760
T3   TGCAAGACATTCTCAAGTCTGACTTTGCCTTTGCATAACAAGCACTTAGCATTAACCCTC
     :  :  :::::   :  :::: ::::: ::  :: :: ::  :: :   :  : :: ::  :::
T7   TCCGTGACATCTTAGAGTCGGACTTCGCGTTCGCGTAAC--GC-CAAATCAATACGACTC

2820
T3   ACTAACGGGAGAC-TACTTAAGGTCTCCCACTTTAAGACACTTTAGGTACTAAGAGATTA
     ::::  :  : ::: :::  ::::::   : :   :    :::::: :
T7   ACTATAGAGGGACAAACTCAAGGTCATTCGCAAGAGTGGCCTTTATGATTGACCTTCTTC
```

SYNTHETIC T7 PROMOTER

5' CGA TAA TAA TAC GAC TCA CTA TAG GGA GA     3'
3' T   ATT ATT ATG CTG AGT GAT ATC CCT CTT CGA 5'

FIG. 6b

SYNTHETIC T3 PROMOTER

5' AATT CAG ATC TCC CTT TAG TGA GGG TTA ATT AGT C 3'
3'      GTC TAG AGG GAA ATC ACT CCC AAT TAA TCA G 5'

PLASMID FOR THE OVERPRODUCTION OF BACTERIOPHAGE T3 RNA POLYMERASE, TRANSCRIPTION VECTORS THAT CARRY A PROMOTER RECOGNIZED BY ITS POLYMERASE, GENE CODING FOR T3 RNA POLYMERASE AND APPLICATION OF THESE PLASMIDS

This invention was made with Government Support under Grant GM-21783 awarded by the National Institute of Health. The Government has certain rights in this invention.

This invention relates to plasmids for the overproduction of bacteriophage T3 RNA polymerase, to transcription vectors which carry a promoter recognized by this polymerase and the use of these vectors in various applications.

The invention also relates to dual RNA polymerase promoters, recombinant DNA vectors which include T3 RNA polymerase promoters, other RNA polymerase promoters, and vectors with T7 and T3 polymerase promoters.

The invention also relates to the gene which codes for the T3 RNA polymerase promoters, vectors thereof, bacteria transformed with such vectors and various applications and other embodiments which will become apparent from the description which follows.

It is known to those skilled in the art that phage RNA polymerase will accurately and efficiently transcribe DNA plasmids carrying promoter sequences recognized by the polymerase thus forming the basis for the manufacture of single stranded RNA probes from plasmids that carry a desirable gene or gene fragment downstream from the promoter. Initial commercial applications for phage RNA polymerases utilized RNA polymerase enzymes produced by bacteriophage SP6. More recently, bacteriophage T7 RNA polymerase has been utilized. The genetic map of bacteriophage T7 is shown in Proc. Natl. Acad. Sci. USA, 82, pp. 1074–1078, February 1985, by Tabor et al. Also see, Watson, Molecular Biology of the Gene, W. A. Benjamin, Inc. 3rd., pps. 426–427.

The use of phage RNA polymerase to produce single-stranded RNA probes requires the presence of a vector (e.g., a plasmid or other double-stranded or partially doublestranded DNA molecule) that contains a promoter sequence recognized by the RNA polymerase and positioned upstream from useful cloning sites in the DNA sequence to be transcribed. Vectors have been constructed which contain T7 or SP6 promoters. While being useful to obtain single strand RNA, it is still necessary to obtain two vectors if RNA complementary to either DNA strand is desired.

There has also been produced a vector containing two promoters. This system contains a T7 promoter and a SP6 promoter flanking a polylinker or multiple cloning site. This vector allows for selective synthesis of RNA from either DNA strand from a single plasmid.

Such plasmids are described, for instance, in a pamphlet of Promega Biotec, Madison, Wis., entitled Riboprobe Gemini. The pamphlet describes a vector constructed using bacteriophage SP6 promoter-containing plasmid pSP64 (Melton, D. A., et al., 1984, Nucleic Acids Research 12, 7035–7056) and a bacteriophage T7 promoter. The resulting plasmid has SP6 and T7 promoters separated by a short piece of DNA containing multiple cloning sites. Another vector has an inverted orientation of restriction sites and was constructed from pSP65 (Melton, supra.).

A pamphlet by United States Biochemical Corporation, Molecular Biology Products, Cleveland, Ohio, entitled GeneScribe describes two plasmids pT7-1 and pT7-2 which include a T7 RNA polymerase promoter immediately adjacent to a polylinker region. The pamphlet shows the restriction maps and the DNA sequences of the promoters and multiple cloning sites. For other details reference is made to that pamphlet, which is incorporated herein by reference.

For other features of this system, reference is made to that pamphlet which is incorporated herein by reference.

Phage RNA polymerases which are necessary to transcribe plasmids are known to be difficult to purify, due in part to difficulty in propagating large scale cultures of phage-infected cells. Thus, it would be advantageous to obtain additional phage RNA polymerases which are easily purified and easily propagated on a large scale.

Accordingly, it is an object of the present invention to provide for a phage polymerase/promoter system which can be used efficiently in the production of RNA.

It is a further object of the invention to provide for a promoter which can effectively be used in conjunction with an additional promoter and a polylinker sequence, thus producing a plasmid which allows for the selective synthesis of RNA from either strand of DNA inserted in the polylinker sequence.

It is a further object of the invention to provide for the production of pure polymerase necessary to activate the promoter.

Two methods for determining a DNA sequence are currently widely used. These are the chemical cleavage method developed by Maxam and Gilbert (sequencing end-labeled DNA with base-specific chemical cleavages, in Grossman, L. and Moldave, K. Eds., Methods in Enzymology, Academic Press, New York, 1979, pp. 499-559) and the chain termination method developed by Sanger.

The method of Maxam and Gilbert uses double-stranded DNA plasmids but is a tedious and time-consuming procedure. The Sanger method requires a single-stranded DNA template and synthetic DNA primers. Further, there are problems associated with pausing by the Klenow fragment of *E. coli* DNA polymerase.

Accordingly, it is a further object of the invention to provide for an improved method of sequence determination.

In accordance with one aspect of the present invention, there is provided a novel vector which includes a first promoter for T3 RNA polymerase, and a second promoter which is a promoter for an RNA polymerase other than T3 RNA polymerase. This vector includes a polylinker segment between the two promoters. The polylinker segment can accomodate a specific DNA segment which is desired to be transcribed, and which is inserted into the polylinker sequence through methods known to those skilled in the art. This vector can be used for the production of RNA, and in particular, RNA probes.

More particularly, in accordance with one of the aspects of the present invention, there is provided a vector containing a dual promoter for RNA polymerase with the promoters being separated by at least one, and preferably more than one restriction enzyme sites, with one of the promoters being a promoter for T3 RNA polymerase. In this manner, a DNA sequence can be inserted between the two promoters and either or both strands of the DNA sequence can be transcribed by selection of the appropriate RNA polymerase.

In accordance with another aspect of the present invention there is provided a gene which encodes the T3 RNA polymerase, and an expression vector which includes such gene. This vector can be used for the production of T3 RNA polymerase.

More particularly, in accordance with the one of the aspects of the present invention, the T3 polymerase gene has been cloned into a high expression plasmid and accordingly, large quantities of the polymerase are synthesized after induction of cells that carry this plasmid.

Recently, a vector of the invention and its advantage over conventional vectors has been described in a pamphlet of Vector Cloning Systems, San Diego, California. The vectors contain strong T3 and T7 bacteriophage transcriptional promoters that display an exceptional degree of specificity for their respective polymerases. Use of the T3 promoter, in contrast to the SP6 promoter, is advantageous because the T3 polymerase gene has been cloned into a high-expression plasmid in *E. coli* yielding large amounts of highly purified enzyme.

The vectors are useful for cloning, sequencing, oligonucleotide mutagenesis, an RNA transcription. For further details one who is skilled in the art is referred to said pamphlet which is incorporated herein by reference.

A better understanding of the present invention as well as other objects and advantages thereof will become apparent upon consideration of the detailed description thereof, especially when taken with the accompanying drawings, wherein:

FIG. 4 is the sequence of the region of T3 DNA that encodes the T3 RNA polymerase, in comparison to the DNA sequence coding for the T7 RNA polymerase; the upper line represents the T3 DNA sequence; the lower line is the T7 DNA sequence. Differences between the two sequences are indicated by asterisks. Important features are indicated by underlining.

Figure 1:
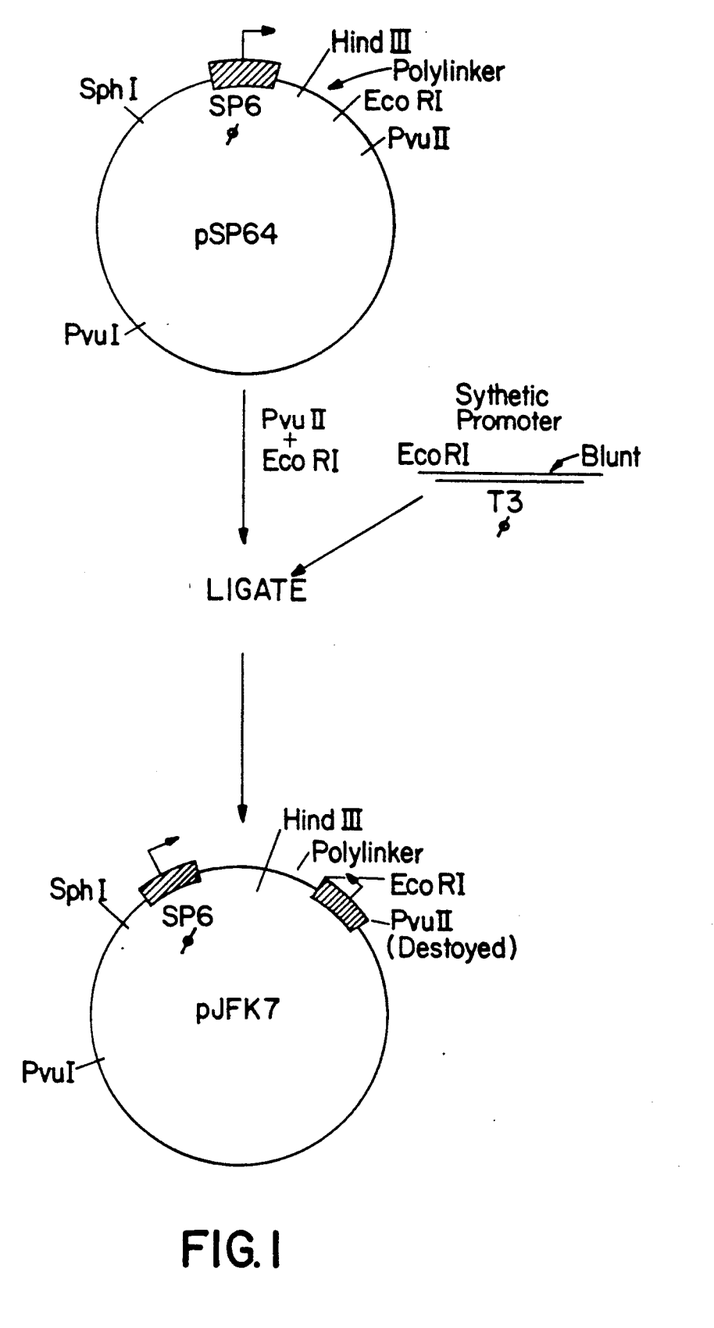
FIG. 1 is a schematic view of the manufacture of a dual promoter plasmid, containing the SP6 and T3 promoter sequences.
Figure 2:
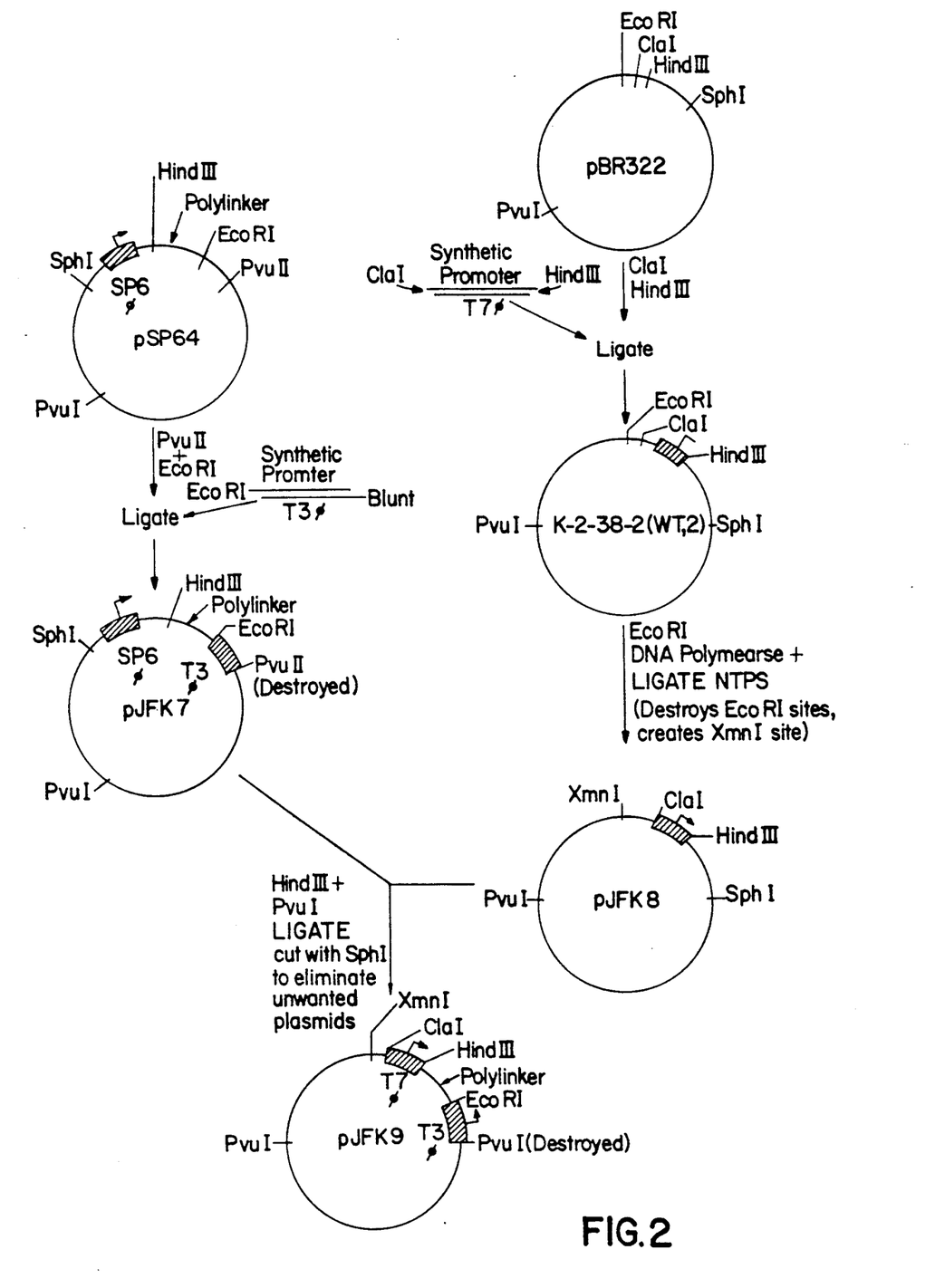
FIG. 2 is a schematic view of the manufacture of a dual promoter plasmid of the invention, containing the T3 and T7 promoter sequences.

The production of vectors containing two promoters for phage RNA polymerase separated by multiple restriction enzyme cleavage sites is schematically shown in FIGS. 1 and 2 and described in detail below. It is to be understood, however, that such description is illustrative and that the scope of the invention extends to vectors other than those specifically shown. In accordance with the invention, the vector can contain different restriction enzyme sites and/or such sites can be in a different sequence; the vector can contain a different number of restriction enzyme sites and can contain other known phage promoter sequences like the several T7's, SP6, gh-1 or other to be developed polymerase promoters, provided one is for T3 RNA polymerase.

Figure 3:
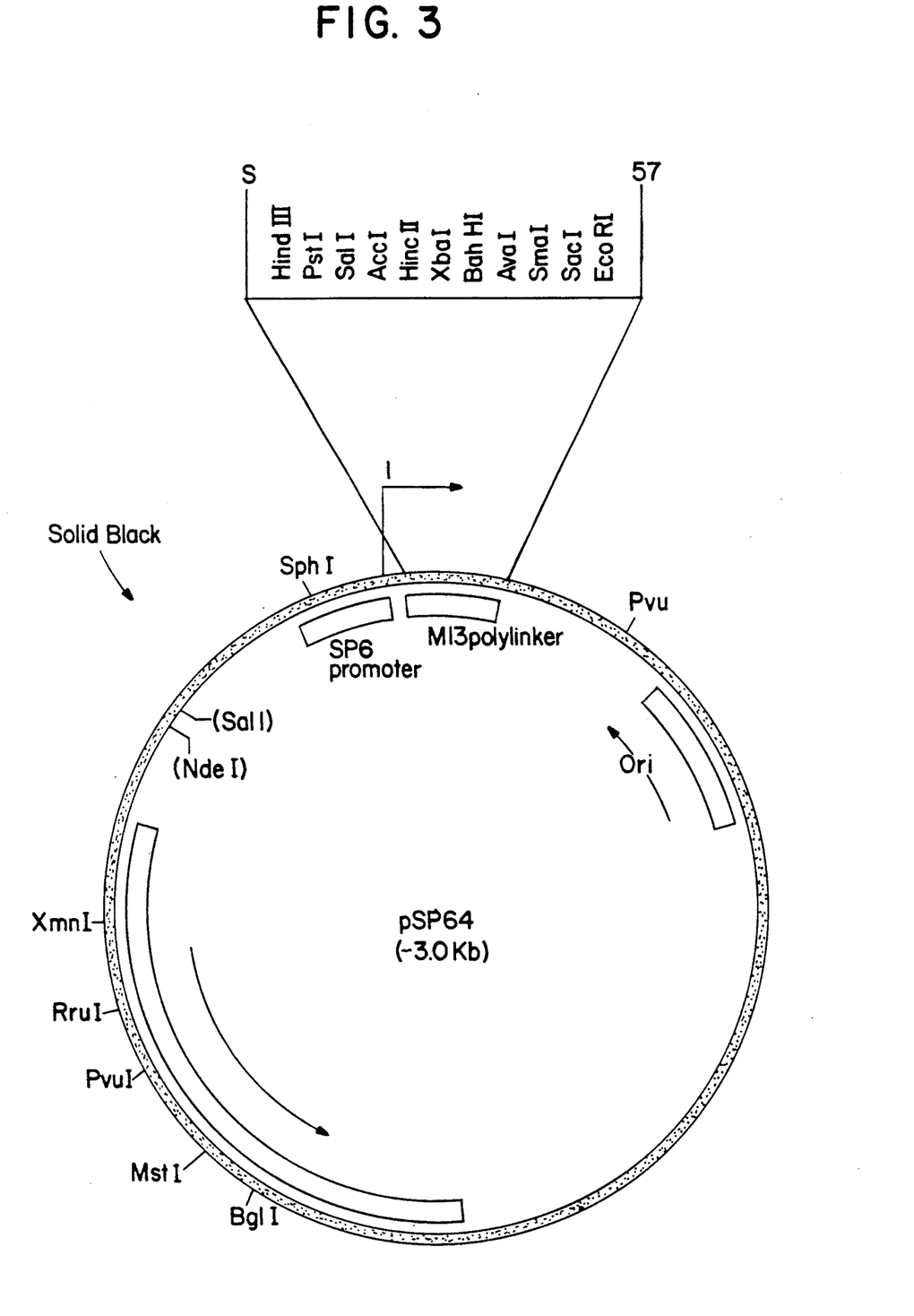
FIG. 3 is a schematic diagram of the expression vector, pSP64.

Referring to FIG. 1 of the drawings, there is shown a schematic procedure for producing the vector containing both the SP6 RNA polymerase promoter and the T3 RNA polymerase promoter, this vector has been designated as pJFK 7. Vector pSP64, available from Promega Biotec Inc., includes the SP6 promoter, as well as a polylinker sequence. The vector is shown in detail in FIG. 3. In accordance with an aspect of the invention, vector pSP64 is modified to produce a novel vector designated pJFK 7, which includes the T3 promoter sequence and the polylinker of pSP64. As more particularly described below, pJFK 7 is produced by cleaving pSP64 with the restriction enzymes Pvu II plus EcoRI, and inserting the synthetic T3 promoter DNA sequence, which includes an EcoRI restriction site at the three prime end and a blunt five prime end.

In accordance with the invention, a T3 promoter DNA consensus sequence is synthesized. The T3 promoter sequence is synthesized on an automated oligonucleotide synthesizer and has the sequence shown in FIG. 6. This sequence represents the "consensus" sequence as derived from eleven known T3 promoters. The sequence of the individual T3 promoters and of the consensus sequence is described in the Table further below. For each position of any single promoter, the particular residue that prevails in that position among the promoters characterized is the consensus residue. All known T3 promoters are within the scope of the invention, and because not all positions need to be preserved, other sequences which are responsive to T3 polymerase, i.e. consensus sequences, are also within the scope of the invention. Thus, the invention includes equivalent consensus sequences which perform equivalent function with respect to T3 polymerases. It is also within the scope of the invention to add additional nucleotides on either end of the promoter sequence. The term "consensus" sequence or residue is known to one skilled in the art.

The sequence of the eleven T3 promoters is as follows:

TABLE

| Map Position (T3 Units)[a] | Nucleotide Position |
|---|---|
| | −10　　　　　　+1 |
| 1.2 | GTC TATTTACCCTCACTAAAGGGAAT AAGG |
| 14.3 | TAG CATTAACCCTCACTAACGGGAGA CTAC |
| 14.7 | TAC AGTTAACCCTCACTAACGGGAGA GTTA |
| 16.1 | AAG TAATAACCCTCACTAACAGGAGA ATCC |
| 19.5 | GGG CATTAACCCTCACTAACAGGAGA CACA |
| 22.8 | GCC TAATTACCCTCACTAAAGGGAAC AACC |
| 44.5 | TAC AATTAACCCTCACTAAAGGGAAG AGGG |

TABLE-continued

| Map Position (T3 Units)[a] | | Nucleotide Position |
|---|---|---|
| 51.5 | | TCT AATTAACCCTCACTAAAGGGAGA GACC |
| 54.2 | | ACC TAATTACCCTCACTAAAGGGAGA CCTC |
| 64.8 | | GTG AATTAACCCTCACTAAAGGGAGA CACT |
| 98.0 | | TTG CATTAACCCTCACTAAAGGGAGA GAGG |
| CONSENSUS[b] | T3 | TATTAACCCTCACTAAAGGGAGA |
| | |         | | | |
| | T7 | TAATACGACTCACTATAGGGAGA |

[a]The approximate positions of the promoters are given in T3 units from the left end of the molecule.
[b]The consensus sequencing for T3 promoter is derived from this work and previous publications. The T7 consensus sequencing is derived from the 17 promoters recognized by the polymerase. Solid vertical lines connect to positions where the 2 promoter sequences always differ from one another; dashed lines connect to positions that are sometimes (but not always) different.

The sequence is described (and the references cited in these publications and references) in Nucleic Acids Research, Vol. 13, 6753 (1983) incorporated herein by reference.

In FIG. 2, there is shown a procedure for producing a vector containing the promoters for T7 and T3 RNA polymerase separated by a polylinker sequence containing appropriate restriction enzyme sites.

As shown, vector pBR322 is modified to include a T7 promoter sequence, and as modified, is designated K-2-38-2(WT,2).

Figure 6A:
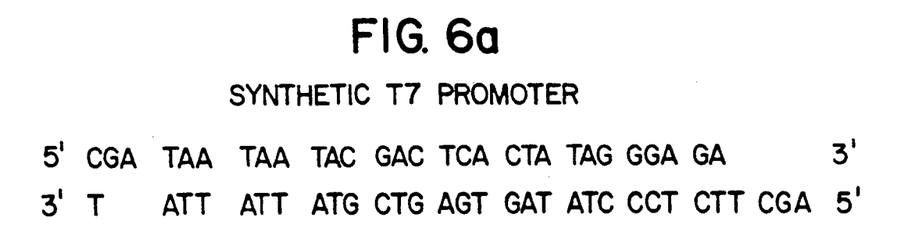
FIG. 6 is the sequence for synthetic T3 and T7 promoters.
Figure 6B:
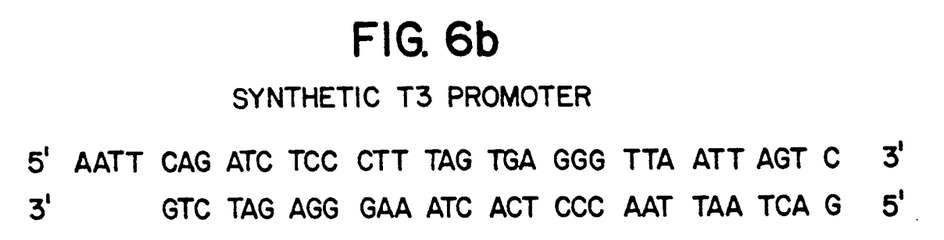

As more particularly described below, vector K-2-38-2 (WT,2) is produced by cleaving pBR322 with the restriction enzymes Cla I and Hind III, and inserting a synthetic T7 promoter sequence having a Cla I restriction site at the three prime end, and a Hind III restriction site at the five prime end. The sequence of the particular T7 promoter used is shown in FIG. 6. The two DNA strands of the synthetic promoter are synthesized on an automated oligonucleotide synthesizer, annealed together and ligated into the Hind III and Cla I sites of the vector by methods known to those skilled in the art.

The EcoRI restriction site is removed from the expression vector K-2-38-2 (WT,2) by cleavage with restriction enzyme EcoRI and subsequent incubation with T4 DNA polymerase in the presence of deoxynucleoside triphosphates by the method of Maniatis et al. (Maniatis, T., Fritsch, E. F., Sambrook, J., *Molecular Cloning: A Laboratory Manual,* Cold Spring Harbor Press, Cold Spring Harbor, N.Y., 1982, incorporated herein by reference). The novel vector, designated pJFK8 is obtained by ligating the resulting blunt-ended vector. An Xmn I site is created where an EcoRI site previously existed.

In accordance with the invention, the dual promoter vector which contains both the T7 and T3 polymerase promoter sequences, pJFK7 and pJFK8 are modified separately or in combination to yield the novel dual promoter plasmid, designated as pJFK9. This plasmid is shown in FIG. 2.

One procedure to make pJFK9 is to modify the above vectors, pJFK7 and pJFK8 by cleaving with restriction enzymes Hind III and Pvu I. Ligation of the resulting fragments with a suitable ligase, such as T4 ligase, results in a mixture of plasmids. Cleavage of the mixture with restriction enzyme Sph I eliminates the unwanted recombinant plasmids. Among the remaining products is found the novel plasmid pJFK9, which contains T7 and T3 promoter sequences, and the hereinabove described polylinker segment.

The plasmid is identified by the fact it is cleaved by restriction enzymes Xmn I, Pvu I and Hind III and transcribed by T7 and T3 polymerases in vitro.

Although the production of a dual promoter vector has been described with reference to the procedure shown in FIGS. 1 and 2 of the drawings, it is to be understood that other such procedures are equally applicable for producing vectors containing T3 and a different RNA polymerase promoter than the one particularly described. It is within the scope of the invention that any polylinker sequence other than the one particularly described in the examples can be employed between the two promoters. Similarly, for example, the restriction enzyme sites of the polylinker as particularly shown can be reversed (as is known for instance comparing vector made from pSP6, and pSP65), and/or other restriction enzymes can be appropriately provided. It is also within the scope of the invention that the linker sequence between the two promoters contain only one restriction site or fewer sites than are in the polylinker sequence described in the examples.

The polylinker used in the invention is described for instance by Norrandes et al., in Gene, 26, 101 (1983), which is incorporated herein by reference.

It is understood that such variations are within the scope of the invention, which provides in one of its important embodiments, a vector having T3 and another RNA polymerase promoter.

The dual promoter vector of the invention are useful and employed to synthesize RNA probes or other RNA products from a DNA sequence which is inserted between the two promoters. To accomplish this objective, the vector is incubated in a reaction mixture that contains phage RNA polymerase, in the presence of a suitable buffer, salts and substrates, such as radiolabeled or biotin-substituted ribonucleotidetriphosphates. By employing the dual vector of the invention, it is possible to synthesize RNA complementary to either one of the strands of the inserted DNA fragment by use of RNA polymerase corresponding to one of the promoters like T3 and to produce RNA complementary to the second strand of the inserted DNA fragment by use of RNA polymerase corresponding to the other promoter.

The vectors of the invention containing dual promoters are particularly suitable for producing RNA probes wherein the RNA that is synthesized contains an appropriate detectable label. Representative examples of detectable labels include radioisotopes, fluorescent materials, and biotin substituted ribonucleosides.

The RNA probes produced by use of the vectors of the present invention are employed as generally known in the art. For example, such an RNA probe may be used as a substrate for RNA modifying enzymes, hybridization probes for detecting homologous or related DNA or RNA sequences, "anti-sense" messenger RNA to specifically inhibit expression of certain gene products, as templates for in vitro translation systems, or as templates for making DNA copies of RNA.

In accordance with another aspect of the present invention, as hereinabove noted, there is provided a gene which encodes T3 RNA polymerase, and the vector in which the gene is inserted. Shown in FIG. 4 is the sequence of T3 DNA.

In accordance with the invention, it has been discovered that the DNA region that encodes the T3 RNA polymerase comprises nucleotides 143 through 2797 as numbered in FIG. 4. In addition, it has been found that cloning of such a gene is most successfully accomplished by separation of the structural gene from the promoter for T3 RNA polymerase which is located at nucleotides 2810 to 2832. In addition, it has been found that for the successful cloning of the gene for T3 RNA polymerase, it is useful to eliminate the promoter for E. coli RNA polymerase which is located at nucleotides 47 through 76.

To obtain the gene that encodes for T3 RNA polymerase free of the promoter for T3 RNA polymerase and of the promoter for E. coli RNA polymerase, the following procedure is followed.

Figure 5:
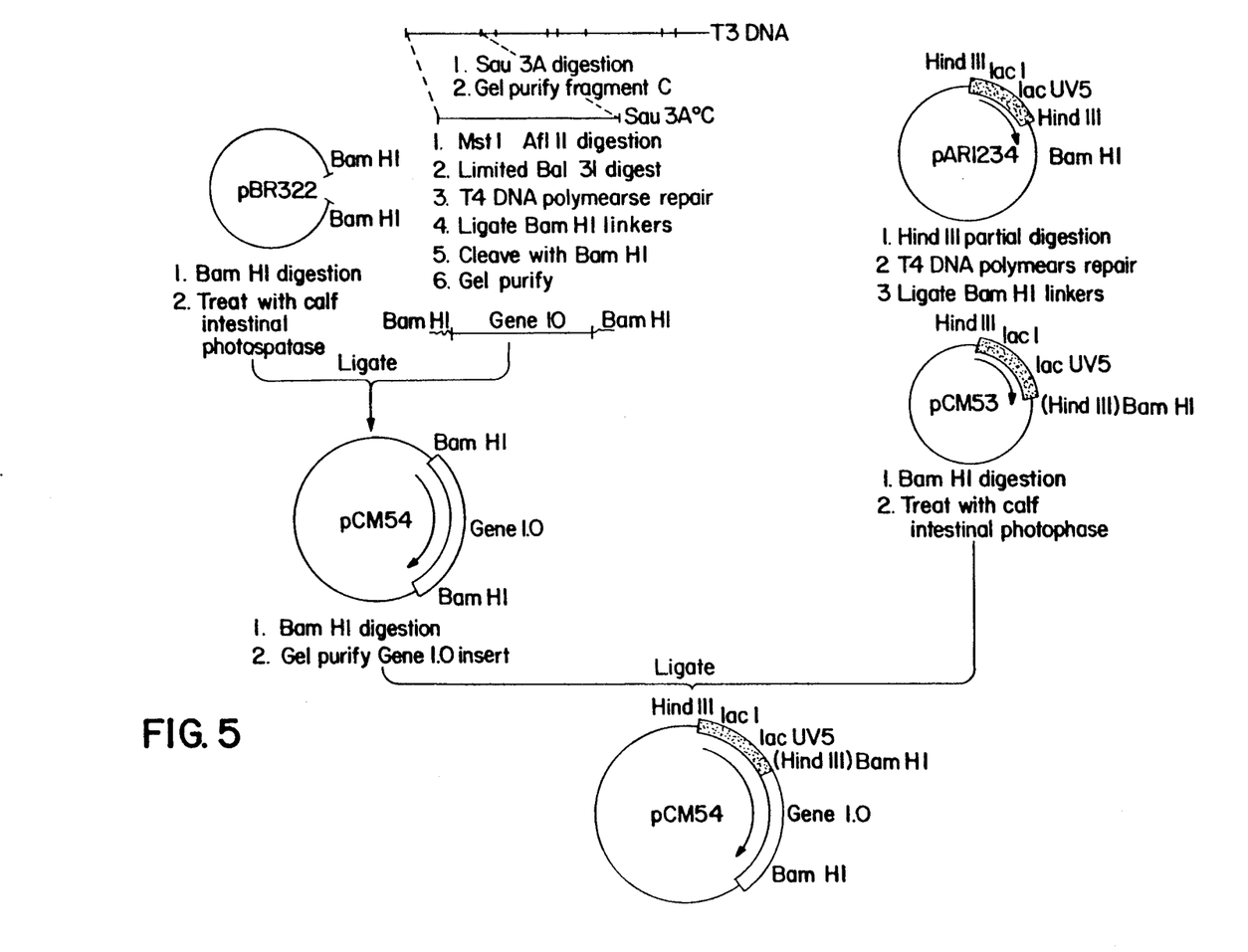
FIG. 5 is a schematic view of the manufacture of an expression vector that carries the structural gene for T3 RNA polymerase under the control of an inducible bacterial transcription control element (Lac UV5)

As shown in FIG. 5, T3 DNA isolated from phage particles is cleaved with restriction enzyme Mbo I. A fragment of 5.9 kb, i.e. the Mbo I-C fragment, which contains the T3 RNA polymerase gene is purified. This fragment is subsequently digested with the restriction enzymes Mst I and Afl II and subjected to limited digestion with the double strand specific exonuclease Bal 31. The extent of Bal 31 digestion is empirically chosen to be sufficient to remove the above mentioned T3 RNA polymerase promoter and the promoter for E. coli RNA polymerase. The ends of the resulting DNA fragments are repaired with T4 DNA polymerase, and synthetic Bam HI linkers are attached by means of T4 DNA ligase. The modified fragment is cleaved with Bam HI and purified by polyacrylamide gel electrophoresis. It is subsequently cloned into an expression vector, pCM 53, by methods known to those skilled in the art, to result in plasmid pCM 56.

Although the invention has been described with respect to the production of a specific vector containing the code for T3 RNA polymerase, it is to be understood that the gene code for T3 RNA polymerase can be inserted into other expression vectors. The selection of other expression vectors, and the insertion of the DNA code for T3 RNA polymerase is deemed to be within the skill of those in the art from the teachings herein.

In accordance with the invention, it is preferred to select a host for transformation which is free of enzymes which can cleave the RNA polymerase. While for convenience E. coli BL21 is selected any other host devoid of such activity is quite suitable.

The expression of RNA polymerase from a plasmid which contains the gene which encodes for T3 RNA polymerase, (preferably free of the two promoters described above) is carried out as follows.

For the expression of RNA polymerase from the plasmid hereinabove described i.e. pCM56, the plasmid is first placed into the host strain E. coli BL21 to produce the strain pCM56/BL21. The host cells are first rendered competent to take up DNA by methods known to those skilled in the art. (See Maniatis et al ). The BL21 host is selected because it is deficient in proteolytic activity that might otherwise lead to cleavage of the purified enzyme. Expression of the T3 RNA polymerase in this host cell is accomplished by the addition of the gratuitous inducer isopropyl-B-D-thiogalactoside (IPTG) to a final concentration of $10^{-4}$ molar in the medium. After 4 hours of induction at 37° C., the cells are harvested and lysed by treatment with lysozyme. The enzyme is then purified by a combination of selective salt precipitation, gel permeation chromatography, ion-exchange chromatography and affinity chromatography by methods known to those skilled in the art. Other known methods are also suitable.

Strain pCM56/BL21 was deposited at the ATCC, 12301 Parklawn Drive, Rockville, Md. on July 24, 1985 and has received ATCC designation 53202.

As noted above, expression of T3 RNA polymerase is performed in accordance with the invention, in any host microorganism bacteria, (encaryotic or procariotic), yeast, etc. For instance, useful host cells include Streptomicae, Bacilliae, other known strains. Preferably, as discussed, the strain selected is free of the protease activity. Thus, it is within the scope of this application to express the T3 RNA polymerase in cells other than E. coli by methods known to those skilled in the art. Successful expression of the gene in yeast has been likewise carried out.

Another noteworthy aspect of the invention provides for an in vivo expression system in which the gene to be expressed is under the control of the RNA polymerase promoter. In this manner, the gene can be produced in abundant quantities. Also for this purpose any host microorganism can be used.

The high specificity of the phage polymerases, and the accuracy with which they initiate transcription, allows a new method of DNA sequence analysis.

The DNA to be sequenced is placed into a plasmid downstream of a phage promoter. The plasmid is then transcribed by the phage RNA polymerase in the presence of specific chain terminators. Suitable are ribonucleoside triphosphate analogs that are incorporated into the growing transcript by the phage RNA polymerase. Once incorporated, they prevent further elongation of the nascent chain. For example, if a chain terminating analog of ATP is used a collection of transcripts that are terminated wherever the DNA has directed the incorporation of an AMP analog will result. These chains can be resolved by gel electrophoresis, resulting in a "A" ladder that permits the determination of the position of all thymidine residues in the DNA template. Use of GTP, CTP and UTP analogs provides similar ladders for the other three bases. Two chain terminating analogs—the 3' deoxyribonucleoside triphosphates (for example, cordycepin triphosphate) and the 3'-O-methyl ribonuceloside triphosphates have been found to be particularly suitable.

The advantages of this method of sequence determination over the Sanger and Maxam and Gilbert methods are as follows:

a. Double-stranded vectors can be used with no need to develop a library in single strand cloning vectors such as an M13 library. The transcription vectors can be plasmids or linear DNAs (such as bacteriophage lambda vectors).

b. Use of dual promoter vectors (e.g., T3/T7 vectors) permits independent sequence determination from both DNA strands—an important requirement for accurate sequence determination.

c. No synthetic DNA primers are required (as they are in the Sanger method). The polymerase initiates transcription directly from promoters present in the plasmid.

d. Because phage RNA polymerases do not terminate on most DNA templates (the phage termination signals are highly specific, and occur extremely rarely in most DNA molecules) problems associated with pausing by the Klenow fragment of *E. coli* DNA polymerase in the Sanger method are eliminated.

e. The same plasmids that are used for DNA sequence analysis may be used to generate RNA probes for structural or diagnostic procedures.

The following examples further illustrate and also present a preferred embodiment of the invention disclosed herein. The examples are not to be construed as a limitation on the scope of the invention. One skilled in the art will be able without undue experimentation to modify or make variants of the invention as he may desire.

EXAMPLE I

Construction of pJFK7

Two micrograms of plasmid pSP64 were digested in a reaction volume of 20 ul containing 10 mM Tris-HCL pH 7.4, 10 mM MgCl$_2$, 1 mM dithiothreitol (DTT), 0.3 mM Spermidine-HCL, 50 mM NaCl (medium salt buffer) and 6 units of the restriction endonuclease Pvu II. After 1 hour at 37° C. the reaction mixture was heated to 65° C. for 5 minutes. Sodium chloride was added to the reaction mixture to a final concentration of 100 mM, and 5 units of the restriction endonuclease EcoRI were added. Calf intestinal phosphatase (CIPase, Boehringer-Mannheim, 0.2 units) was added and the reaction mixture was incubated at 37° C. for 30 minutes. To inactivate the CIPase, trinitriloacetic acid (TNA) pH 7.7 was added to a concentration of 7 mM and the reaction was heated to 65° C. for 20 minutes. The reaction mixture was extracted with phenol (Maniatis et al, op cit.), and the nucleic acids were precipitated by the addition of 2.5 volumes of 95% ethanol at −70° C. for 15 minutes. The pellet was washed twice in 100 ul of 70% ethanol at −20° C., dried in vacuo, and resuspended in 20 ul of 0.01 M Tris-HCl, pH 7.4; 1 mM EDTA (TE).

Two hundred nanograms of plasmid pSP64 digested as described above were ligated with 2 ul of synthetic oligomers numbers 7 and 8 which have been annealed (see Example X) in a volume of 20 ul containing 50 mM Tris HCl pH 7.4, 10 mM MgCl$_2$, 10 mM DTT, 1 mM Spermidine-HCl, 1 mM ATP, 0.1 mg bovine serum albumin (BSA), 0.5 units of T4 DNA ligase (Boehringer-Mannheim) at 16° C. for 12 hours. The reaction mixture was heated to 65° C. for 5 min. Twenty nanograms of the reaction mixture were added to 100 ul of competent bacterial (strain HB101) prepared by the method of Hanahan et al [J. Mol. Biol. 166:557–580 (1983)]. Transformants were screened for the presence of a plasmid having a single Bgl II site that was present only in the synthetic oligomer. The resulting plasmid is designated pJFK7.

The plasmid was characterized by determining that the plasmid contained SP6 and T3 promoters oriented in opposite directions with a polylinker between the two promoters. This was done by determining that the promoters and the polylinker had the desired level of activity. In addition a direct sequence determination of the promoter sequence was carried out.

EXAMPLE II

Construction of K-2-38-2 (WT2)

Twenty ug of the plasmid pBR322 were digested with 20 units of restriction endonuclease Hind III (Boehringer-Mannheim) in the medium salt buffer described above at 37° C. for 1 hour. The reaction mixture was terminated by heating to 65° C. for 10 minutes, and one unit of CIPase was added. The reaction mixture was further incubated at 37° C. for 15 minutes, extracted with phenol and chloroform-isoamylalcohol as previously described (Maniatis et al). The nucleic acids were precipitated by the addition of sodium chloride to a concentration of 0.1 M and 2.5 volumes of 95% ethanol. The pellet was washed twice with 70% ethanol, dried in vacuo, and resuspended in 40 ul TE.

Two micrograms of the pBR322 plasmid digested as described above were further digested with the restriction endonuclease Cla I (Boehringer-Mannheim) in low salt buffer (10 mM Tris HCl, pH 7.4; 10 mM MgCl$_2$; 1 mM DTT; 0.3 mM spermidine-HCl) for 1 hour at 37° C. The sample was treated with 0.38 units CIPase, extracted with phenol, and precipitated with ethanol as described above. The nucleic acids were resuspended in 20 ul of distilled water.

0.2 ug of the plasmid digested as described above were incubated with 22.5 nanograms of annealed synthetic oligomers numbers 1 and 2 (see Example X) in the presence of 0.18 units of T4 DNA ligase in the ligase buffer described above at 4° C. for 12 hours. A sample of the ligation mixture containing 10 nanograms of nucleic acid was used to transform 100 ul of competent cells (HB101, see above). DNA from 28 transformants was isolated by the rapid alkaline extraction protocol (Maniatis et al, op cit.). To detect the presence of the desired plasmid, DNA was digested with the restriction endonuclease Bam HI in medium salt buffer, both for 1 hour for 37° C. The resulting digestion mixtures followed by digestion with EcoRI in high salt buffer (same as low salt buffer, except that it contained 100 mM naCl) were analyzed by electrophoresis in 5% polyacrylamide gels. Because the desired plasmid has an Hinf I recognition site within the synthetic DNA region, extracted DNA was also digested with the restriction endonuclease Hinf I in medium salt buffer and also analyzed by polyacrylamide gel electrophoresis. Plasmid DNA having the desired characteristics was used to transform competent HB101 cells as described above. One subclone (#2) of clone #38 was subsequently chosen at random, characterized and found to have the desired plasmid designated as K-2-38-2 (WT,2) in FIG. 2.

The structure of the plasmid was verified by translating the plasmid in vitro with T7 polymerase and by direct sequence determination of the region between the EcoRI and Hind III sites.

EXAMPLE III

Construction of pJFK8

Five micrograms of K-2-38-2 (WT,2) was digested with 15 units EcoRI in the high salt buffer described above at 37° C. for 1 hour. The reaction was inactivated by heating to 65° C. for five minutes. 1.5 ug of digested plasmid DNA was incubated with T4 DNA polymerase in a reaction of 40 ul containing 0.125 mM of all four deoxyribonucleotidetriphosphates, 5 units of T4 DNA polymerase (PL Biochemicals), 33 mM Tris-Acetate pH 7.9, 66 mM potassium acetate, 10 mM Mg acetate, 0.5 mM DTT, 0.1 ml bovine serum albumin at 37° C. for 45 minutes. Forty ul of TE were added and the sample was extracted with phenol and precipitated with ethanol as described above. The nucleic acids were resuspended in 40 ul of TE. Eighty nanograms of the repaired DNA were incubated with 0.5 units of T4 DNA ligase in the ligation buffer described abouve at 16° C. for 12 hours. After the ligation, 40 nanograms of the DNA were digested with EcoRI in the high salt buffer described above, at 37° C. for one hour, and 20 nanograms were used to transform competent HB101 cells. Plasmid DNA in ten transformants was screened by digestion with the restriction endonucleases EcoRI and Bam HI; all of them had the desired characteristics of having single restriction sites for each enzyme. One of these was chosen at random for further study and was designated pJFK8. As a result of the manner in which the EcoRI site was repaired with T4 DNA polymerase and the subsequent blunt end ligation, an Xmn I site was created at the site previously occupied by the EcoRI site. This was verified by digestion with XmnI and EcoRI.

EXAMPLE IV

Construction of pJFK9

Fifteen ul cultures of HB101/pJFK8 and HB101/pJFK8 were propagated overnight in nutrient broth containing 50 ug ampicillin. Plasmid DNA was extracted from the cultures by the rapid alkaline procedure described above. The DNA pellet was washed twice with 1 ml 70% ethanol, resuspended in 250 ul of TE, phenol extracted as described above, precipitated and suspended in 25 ul TE. One microgram of each plasmid DNA preparation was digested with the restriction endonuclease Hind III in 20 ul of medium salt buffer at 37° C. The salt was adjusted to 100 mM sodium chloride and 3.5 units of the restriction endonuclease Pvu I were added and incubation was continued at 37° C. for 1 hour. The samples were extracted with phenol, precipitated with ethanol and resuspended in 10 ul of TE as described above.

0.2 ug of each of the digested plasmid DNAs were mixed together and incubated in a ligase reaction of 20 ul containing 0.5 units T4 ligase and the ligase buffer described above at 16° C. for 12 hours. After incubation, the salt was adjusted to 150 mM sodium chloride, and 2.5 units of the restriction endonuclease Sph I was added. The reaction mixture was incubated at 37° C. for 1 hour, heated to 65° C. for 5 minutes, and 40 nanograms of the nucleic acids were used to transform competent HB101 cells. Plasmid DNA from resulting transformants was extracted by the rapid alkaline extraction protocol and characterized by digestion with either Bgl II and Pvu I or Pvu I and Sph I. One plasmid with the desired characteristics of having T3 and T7 promoter sequences on opposite sides of the polylinker was chosen and designated as pJFK9.

The characteristics of pJFK 9 were verified by digestion with restriction endonucleases and by transcribing DNA in vitro with T3 and T7 RNA polymerases.

EXAMPLE V

Isolation, cloning, expression and purification of the gene for T3 RNA polymerase DNA isolated from T3+ phage particles was cleaved with Sau 3A and purified by electrophoresis through a 0.8% agarose gel. Fragment C (5450 bp) was isolated by electroelution (Maniatis et al, 1982). Ten micrograms of this DNA were cut with Mst I and Afl II [which recognize sites 133 bp upstream and 38 bp downstream from the start and stop codons, respectively (see FIG. 2)]. The mixture of fragments was then subjected to limited digestion with the double-stranded specific exonuclease Bal 31 under conditions specified by the manufacturer (IBI). The reaction was terminated at time points varying between 2-27 minutes by adding ethylene glycol-bis (B-amino ethyl ether ) N,N,N,-tetraacetic acid (EGTA) to 20 mM. The mixture of Bal 31 treated fragments was extracted with phenol and precipitated with ethanol. The DNA pellet was taken up in 40 ul buffer (33 mM Tris.HCl, pH 7.9; 66 mM MgCl$_2$; 0.5 mM DTT; and 100 ug/ml gelatin) and incubated with 5 units T4 DNA polymerase and deoxynucleotide triphosphates (0.25 mM each) for 45 minutes at 37° C. The reaction was terminated by heating at 65° C. for 5 minutes. Synthetic Bam HI linkers were ligated to the ends of the DNA by incubation for 16 hours at 13° C. with 2 units of T4 DNA ligase under conditions specified by Maniatis et al (1982). The reaction was terminated by heating at 65° C. for 5 minutes, and extracted with phenol. After precipitation with ethanol, the DNA was incubated with Bam HI to cleave the linkers. The resulting mixture was applied to a 5% polyacrylamide gel, and DNA in the size range of 2700 bp was eluted by the procedure of Maxam and Gilbert (1979). The resulting DNA was ligated with pBR322 DNA that had been cleaved with Bam HI and treated with calf intestinal phosphatase (BRL). The ligated DNA was transformed into competent HB101 cells (Hanahan, 1983). Transformants were screened, first for the presence of a plasmid having a Bam HI insert of the appropriate size (2.7 kb) and second, for the presence of RNA polymerase activity in an in vitro assay (see Example VI below). A clone having a plasmid with both characteristics (pCM54) was identified.

To express the phage RNA polymerase, the coding region was removed from pCM54 by cleavage with Bam HI and cloned into pCM53. The plasmid pCM53 carries the inducible lac UV5 promoter along with the lacI gene in the Hind III-Bam HI sites of pBR322. Plasmid pCM53 was derived from pAR1234 (Davanloo et al, 1984) by converting the rightmost Hind III site in pAR1234 to a Bam HI site by insertion of a synthetic linker, digesting with Bam HI, and religating the plasmid. This eliminated the 346 bp fragment that intervened between the original Hind III and Bam HI sites in pAR1234. Cleavage of pCM53 with Bam HI and insertion of the coding region at the Bam HI site downstream of the promoter produced the plasmid pCM56. Thus, pCM56 has Bam HI site downstream from the lac UV5 promoter.

pCM56 was transformed originally into HB101. Subsequently, the plasmid was moved into *E. coli* strain BL21.

Cultures of pCM56/BL21 were propagated at 37° C. in M9TB medium (Studier, Virology, 39:562-574, 1969) containing 50 ug/ml of ampicillin. When the optical density reached 0.8 at 600 nm, the cultures were induced by the addition of isopropyl-D-thiogalactoside (IPTG) to 0.4 mM. After four hours, the cultures were combined and the cells were harvested by centrifugation (5000×g, 10 min). The cell pellet (8 gm) was washed once with 400 ml of cell suspension buffer (50 mM Tris.HCl, pH 8.0, 20 mM naCl; 2 mM EDTA; 1 mM DTT), resuspended in 24 ml of buffer, frozen in a dry ice/ethanol bath and stored at −70° C.

Frozen cells were thawed at room temperature and placed at 4° C. Lysis was accomplished by incubating in the presence of 9 mg of lysozyme (Calbiochem) for 20 minutes followed by incubation with deoxycholate (0.05% w/v) for 20 minutes. The vicosity was reduced by incubating with 10 mM MgCl$_2$ and 50 ug/ml DNase (Worthington) for 20 minutes. The volume of the lysate was adjusted to 45 ml with cell suspension buffer, and 5 ml of 2M ammonium sulfate were slowly added. After 10 minutes, the lysate was clarified by centrifugation at 10,000×g for 20 minutes. Polyethyleneimine (BDH Chemicals, Ltd., 10% v/v, pH 7.8) was slowly added to the supernatant to a concentration of 0.5%. After 10 minutes the mixture was clarified by centrifugation. The supernatant was brought to 55% saturation by the slow addition of a saturated ammonium sulfate solution, and incubated at 0° C. for 10 minutes. The precipitate was collected by centrifugation and resuspended in a minimal volume of column buffer (20 mM potassium phosphate, pH 7.7; 1 mM EDTA, 1 mM DTT, 5% glycerol) containing 100 mM NaCl. The sample was dialyzed overnight against two 1 liter changes of this buffer.

The dialysate was clarified by centrifugation and applied to a phosphocellulose column (Whatman P-11, 2.5 cm×7 cm) equilibrated with buffer containing 200 mM NaCl. The column was washed with 5 volumes of starting buffer, and RNA polymerase was eluted with buffer containing 750 mM NaCl. Column fractions were assayed for T3 RNA polymerase by transcription assays and by Coomassie blue staining of column fraction samples spotted on filter paper (described below). At this point, the T3 RNA polymerase was the major protein in the eluate and the Coomassie blue staining of protein spots was sufficient to assay for polymerase in subsequent steps. Peak fractions were pooled and dialyzed vs. two 1 liter changes of buffer containing 25 mM NaCl for 1.5 hours each. The dialysate was diluted to a conductivity corresponding to buffer containing 25 mM NaCl, and applied to a TSK-CM column (EM Science, 2.5 cm×5 cm) equilibrated with buffer containing 25 mM NaCl. The column was washed with 10 volumes of starting buffer, and T3 RNA polymerase was recovered in the wash fractions. Peak fractions were pooled and adsorbed to a TSK-DEAE colume (EM Science, 2.5 cm x 3 cm) equilibrated with buffer containing 25 mM NaCl. The column was washed with 5 volumes of starting buffer and the RNA polymerase was eluted with buffer containing 75 mM NaCl. Peak fractions were pooled and stored on ice. This method yielded 20 mg of essentially pure T3 polymerase.

EXAMPLE VI

RNA polymerase assays

Samples (usually 2 ul of a 1:1000 dilution of column fractions) were assayed in transcription reactions as described above, except that they also contained 2.5 ug/ml rifampicin (Schwarz/Mann). After incubation for 15 minutes at 37° C., 50 ul were removed and spotted onto 2.5 cm Whatman 3 MM filter paper discs that had been presoaked in 10% TCA, 10 mM sodium pyrophosphate, 1 mM sodium phosphate and dried. Filters were batch washed on ice 5 times in the 10% TCA solution, once in acetone, dried and counted, using scintillation grade toluene containing 4 gm/1 Omnifluor (New England Nuclear).

EXAMPLE X

Synthesis of synthetic oligomers

Four synthetic oligomers were synthesized having the sequences denoted below (reading from 5' to 3').

| Oligomer #1 | CGATAATAATAC(G/C)ACTCACTATAGGGAG |
| Oligomer #2 | AGCTTCTCCCTATAGTGAGT(G/C)GTATTATTAT |
| Oligomer #7 | GACTAATTAACCCTCACTAAAGGGAGATCTG |
| Oligomer #8 | AATTCAGATCTCCCTTTAGTGAGGGTTAATTAGTC |

All oligomers were synthesized on an Applied Biosystems Model 380A automated DNA synthesizer. Synthesis was carried out by the phosphoramidite method according to standard protocols supplied by the manufacturer. At the conclusion of the synthesis, the oligomer was detritylated, deblocked and cleaved from the resin on the machine by the procedures specified by the manufacturer. The samples were further deprotected by incubation in an equal volume of 38% ammonium hydroxide at 50°–55° C. for five hours. The samples were lyophilized to dryness and resuspended in 200 ul of distilled water. Samples were centrifuged for 5 minutes in an Eppendorf microfuge to remove particulate matter, and the supernatant was extracted 2 times with an equal volume of n-butanol saturated with water. Approximately six OD units of the oligomer were mixed with an equal volume of sample buffer (1 mm EDTA, 50 mm Tris-borate, pH 8.3, 80% formamide) and heated to 90° C. for 10 minutes. The sample was loaded onto a 20% polyacrylamide sequencing gel which had been pre-electrophoresed at 5 milliamperes for ½ hour. Electrophoresis was continued at 5 milliamperes until the xylene cyanol marker, which was loaded in an adjacent lane, had migrated 7 cm. The oligomer was viewed on the gel by UV shadowing, and the region of the gel containing the high molecular weight band was cut out with a razor blade. The gel sample was crushed, 1 ml of 0.1 M ammonium bicarbonate was added and incubated at 37° C. overnight. The mixture was centrifuged 5 minutes in an Eppendorf microfuge, and the pellet was washed with 250 ul ammonium bicarbonate (0.1 M) and the supernatants were combined. The combined supernatants were lyophilized to dryness and resuspended in 100 ul of 0.1 M ammonium bicarbonate. The sample was applied to a Sephadex G-50 column (1 cm×16 cm) and the column was eluted with 0.1 M ammonium bicarbonate. One ml fractions were collected, and fractions containing the peak OD material were combined and lyophilized to dryness. The sample was resuspended in 100 ul of distilled water and lyophilized again. This procedure was repeated until no further ammonium bicarbonate was apparent in the tubes. The final sample was resuspended in 100 ul of distilled water and the concentration was determined by the absorbance at 260 nm.

The oligonucleotides were kinased in a 20 ul reaction containing 50 mM Tris-Hcl, pH 7.5, 10 mM MgCl$_2$, 5 mM DTT, 1 mM spermidine, 1 mM EDTA, 1 mM ATP, 4 units kinase and 5 ug of oligonucleotides.

Single stranded oligonucleotides were annealed together and purified by modification of the method of Rossi, J. Biol. Chem. 257:9226 (1982). The oligonucleotides were mixed at a concentration of 1.5 uM in a volume of 40 ul, and the sample was placed in a boiling water bath for 3 minutes and then cooled at room temperature for 30 minutes. One tenth volume of dye buffer (40% glycerol, 0.2 M EDTA, 0.2 mg (ml bromophenol blue) was added and the sample was loaded onto a 20% polyacrylamide/tris-borate gel (1.7 mm thick, 14 cm long, 0.8 cm lane width) The gel was electrophoresed at 250-300V for 2 hrs followed by electrophoresis at 50-150V, until the bromophenol blue marker had reached the end of the gel. The products were visualized by UV-shadowing and eluted by the method of Maxam and Gilbert.

EXAMPLE XI

Sequence analysis

For sequence analysis, reactions (20 ul) contained 20 mM Tris-HCl, pH 7.9; 20 mM MgCl$_2$; 3 mM spermidine-HCl; 1 mM dithiotreitol; 0.125 mM GTP, CTP, UTP and [$\alpha$-$^{32}$P]-ATP (specific activity =8 mCi/umol), 3 units T3 RNA polymerase, 0.9 ug template DNA (circular pJFK1); and inhibitor as indicated. The reactions were incubated at 37° C. for 1 hour and terminated by the addition of 4 ul stop buffer [0.2 M EDTA, yeast tRNA (1 mg/ml Sigma)] and placed on ice. Nucleic acids were precipitated either by the addition of 2.5 volumes 95% ethanol, or 4 volumes 4 M acetic acid (14). After centrifugation (15 min.), the pellets were washed once with 200 ul 2M acetic acid, once with 200 ul 70% ethanol, and dried in vacuo. The samples were taken up in 3 ul sample buffer [7M urea; 50 mM Tris-borate, pH 8.3; 0.1 mM EDTA; bromophenol blue (1 mg/ml); xylene cyanole (1 mg/ml)], heated for 30 sec. in a boiling water bath and chilled rapidly in an ice-water bath. Aliquots (2 ul) of the sample were applied to a 35 cm×43 cm×0.4 mm 8% polyacrylamide gel (acrylamide:bis acrylamide =29:1) made up in a buffer of 1 M Tris-borate, pH 8.3; 0.1 M EDTA; and 8.3 M urea. The runnig buffer was 1 M Tris-borate, pH 8.3; 0.1 M EDTA. Electrophoresis was at constant power, 1600-1800V (sufficient to give a gel temperature of ca 50° C.) for 1.5 hrs. The gels were exposed to Dupont Cronex-4 X-ray film in the presence of a Dupont Cronex screen, at −70° C. for 24-36 hours. A sequencing ladder was obtained.

The present invention is particularly advantageous in that the overproducing expression plasmid pCM56 permits large scale and economic production of T3 RNA polymerase of high purity.

The dual vectors of the invention carrying T7 and T3 are particularly advantageous in that the gene for the T7 RNA polymerase has also been cloned and overexpressed resulting in similar economies and purity for this enzyme as compared with other enzymes such as the SP6 enzyme. Further, the presence of two promoters in opposite orientations on either side of the polylinker permits transcription across the polylinker, including any DNA inserted into the polylinker, in either direction depending upon the choice of the polymerase. This obviates the need to clone the desired fragment twice as would have to be done with single promoter vector.

Additional references that may be useful for one skilled in the art are: Comparison of the Bacteriophage T3 and T7 RNA polymerases by McAllister, et al., Sequence Specificity in Transcription and Translation, Alan R. Liss, New York, N.Y. (1985); other earlier work with T7 is reported by Tabor and Richardson, Proc. Acad. Sci. 82, 1074 (1985) and McAllister et al. in J. Mol. Biol. 153, 527 (1981); Morris et al., Cloning and expression of the bacteriophage T3 RNA polymerase gene, Gene, in press; Klement et al., Sequencing of DNA Using T3 RNA Polymerase and Chain Terminating Ribonucleotide Analogs, Gene, in press.

All references and publications, etc. cited in this application (and the references cited in these publications and references) are incorporated herein by reference.

I claim:

1. A dual phase RNA polymerase promoter vector having a polylinker with a multiple cloning site, which polylinker is linked at one of its ends to a T3 phage promoter which is recognized by and is specific for T3 RNA polymerase and on the other of its ends to a second phage promoter, which is a promoter other than a T3 RNA polymerase promoter, the two promoters being linked in opposite orientation with respect to the polylinker, wherein transcription from either of the phage promoters proceeds toward the other promoter and in a direction opposite from the direction of transcription of the other phage promoter and the phage polymerase capable of transcription from said promoters is specific and does not recognize the other phage promoter, and which second phage promoter is recognized by the other polymerase.

2. The dual polymerase promoter vector of claim 1 wherein the second promoter is selected from the group consisting of a promoter for T7 and SP6 RNA polymerases.

3. The dual polymerase promoter vector of claim 2 wherein the second promoter is a T7 polymerase promoter.

4. The dual RNA polymerase promoter vector of claim 2 wherein the second promoter is an SP6 promoter.

5. The dual phase RNA promoter vector of claim 1 wherein the cloning site contains HindIII and EcoRI restriction sites.

6. A recombinant DNA vector which comprises a polylinker sequence having linked to one of its ends a T3 phage promoter which is recognized by and is specific for T3 RNA polymerase and at the other of its ends, a second phage RNA polymerase promoter, the two promoters being linked in opposite orientation with respect to the polylinker, wherein said second promoter is a promoter other than a T3 phage RNA polymerase promoter and a DNA sequence inserted in the polylinker sequence having a multiple cloning site, the respective promoters being in opposite orientation and the recombinant DNA vector being capable of transcription of DNA to produce RNA strands complementary to either one of the strands of the inserted DNA sequence when there is supplied to the vector a phage promoter-specific polymerase, wherein transcription from either of the phage promoters proceeds toward the other promoter and in a direction opposite from the direction of transcription of the other phage promoter and the phage polymerase capable of transcription from said promoters is specific and does not recognize the other phage promoter, and which second phage promoter is recognized by the other polymerase.

7. The recombinant DNA vector of claim 6 wherein the second promoter is a T7 RNA polymerase promoter.

8. The recombinant DNA vector of claim 6 wherein the polylinker includes restriction sites XmnI and PvuI, positioned between the two promoter sequences.

9. The recombinant DNA vector of claim 6 wherein the T3 RNA polymerase promoter has a consensus sequence recognized by T3 polymerase.

10. The recombinant DNA vector of claim 9 wherein the consensus sequence comprises the following sequence TATTAACCCTCACTAAAGGGAGA.

11. The recombinant DNA vector of claim 6 wherein the cloning site contains HindIII and EcoRI restriction sites.

12. A recombinant DNA vector which comprises a polylinker sequence connected at one end to a SP6 phage RNA polymerase promoter and at the other end to a T3 phage promoter which is recognized by and is specific for T3 RNA polymerase, the two promoters being linked in opposite orientation with respect to the polylinker, wherein transcription from either of the phage promoters proceeds toward the other promoter and in a direction opposite from the direction of transcription of the other phage promoter and the phage polymerase capable of transcription from said promoters is specific and does not recognize the other phage promoter.

13. The recombinant DNA vector of claim 12 wherein the polylinker has an EcoRI restriction site at the end adjacent to the T3 promoter.

14. A recombinant DNA vector of claim 13 wherein the T3 RNA polymerase promoter has a consensus sequence recognized by a T3 polymerase.

15. A kit for genetic applications, especially for transcription of DNA to synthesize RNA transcripts complementary to either strand of a DNA sequence, which kit comprises in combination the following components: a recombinantly produced T3 RNA polymerase, another recombinantly produced phage RNA polymerase and a dual promoter transcription vector having a T3 phage RNA promoter specific for said T3 RNA polymerase and another promoter specific for the other phage RNA polymerase, the respective promoters being linked at opposite ends of a polylinker having a multiple cloning site the two promoters being linked in opposite orientation with respect to the polylinker, wherein transcription from either of the phage promoters proceeds towards the other promoter and in a direction opposite from the direction of transcription of the other phage promoter, each phage promoter being recognized by the phage encoded RNA polymerase which is specific to that phage promoter and does not recognize the other phage promoter, and which second phage promoter is recognized by the other polymerase.

16. The kit of claim 15 wherein the other recombinantly produced phage RNA polymerase is from phage T7.

17. The kit of claim 15 wherein the promoter other than the T3 promoter is selected from the group of promoters consisting of T7 and SP6.

18. The kit of claim 15 wherein the promoter other than T3 is a T7 promoter.

19. The kit of claim 15 wherein the promoter other than T3 is a SP6 promoter.

20. The kit of claim 15 wherein the cloning site contains the restriction sites HindIII and EcoRI.

21. A method for producing in vitro RNA copies of a selected DNA sequence, which comprises the steps of inserting the selected DNA sequence in a polylinker of a recombinant DNA vector, mixing the vector with either one of a T3 phage RNA polymerase or another phage RNA polymerase and generating RNA copies of the inserted DNA sequence, the vector comprising a polylinker sequence containing a restriction site and having linked to one of its ends, a T3 RNA polymerase promoter and on the other of its ends to a second phage RNA polymerase promoter other than a T3 phage RNA polymerase promoter, and transcription proceeding from either of the phage promoters towards the other promoter and in a direction opposite from the direction of transcription of the other phage promoter, the T3 phage RNA polymerase recognizes the second phage RNA polymerase promoter and is specific to that promoter.

22. The method of claim 21 wherein the other RNA polymerase and specific promoter are from phage SP6.

* * * * *